United States Patent
Krishnamurthy

Patent Number: 5,215,758
Date of Patent: Jun. 1, 1993

[54] CONTROLLED RELEASE MATRIX SUPPOSITORY FOR PHARMACEUTICALS

[75] Inventor: Thinnayam N. Krishnamurthy, Ontario, Canada

[73] Assignee: Euroceltique, S.A., Luxembourg

[21] Appl. No.: 758,883

[22] Filed: Sep. 11, 1991

[51] Int. Cl.⁵ .................................................. A61K 9/02
[52] U.S. Cl. ..................................... 424/488; 424/422; 424/436; 424/484; 424/DIG. 15; 514/770; 514/779; 514/786; 514/965; 514/966
[58] Field of Search ............... 424/484, 436, DIG. 15, 424/488

[56] References Cited

U.S. PATENT DOCUMENTS 5,102,666  4/1992  Acharya .............................. 424/487
5,110,605  5/1992  Acharya .............................. 424/487

Primary Examiner—Thurman K. Page
Assistant Examiner—James M. Spear
Attorney, Agent, or Firm—Steinberg & Raskin

[57] ABSTRACT

The controlled release of therapeutically active agents is achieved from a controlled release matrix of sodium alginate and a calcium salt. When the composition is to be administered rectally, the matrix is combined with a therapeutically active agent and a suitable suppository base. When the composition is to be administered orally, the matrix further includes a higher aliphatic alcohol.

13 Claims, 1 Drawing Sheet

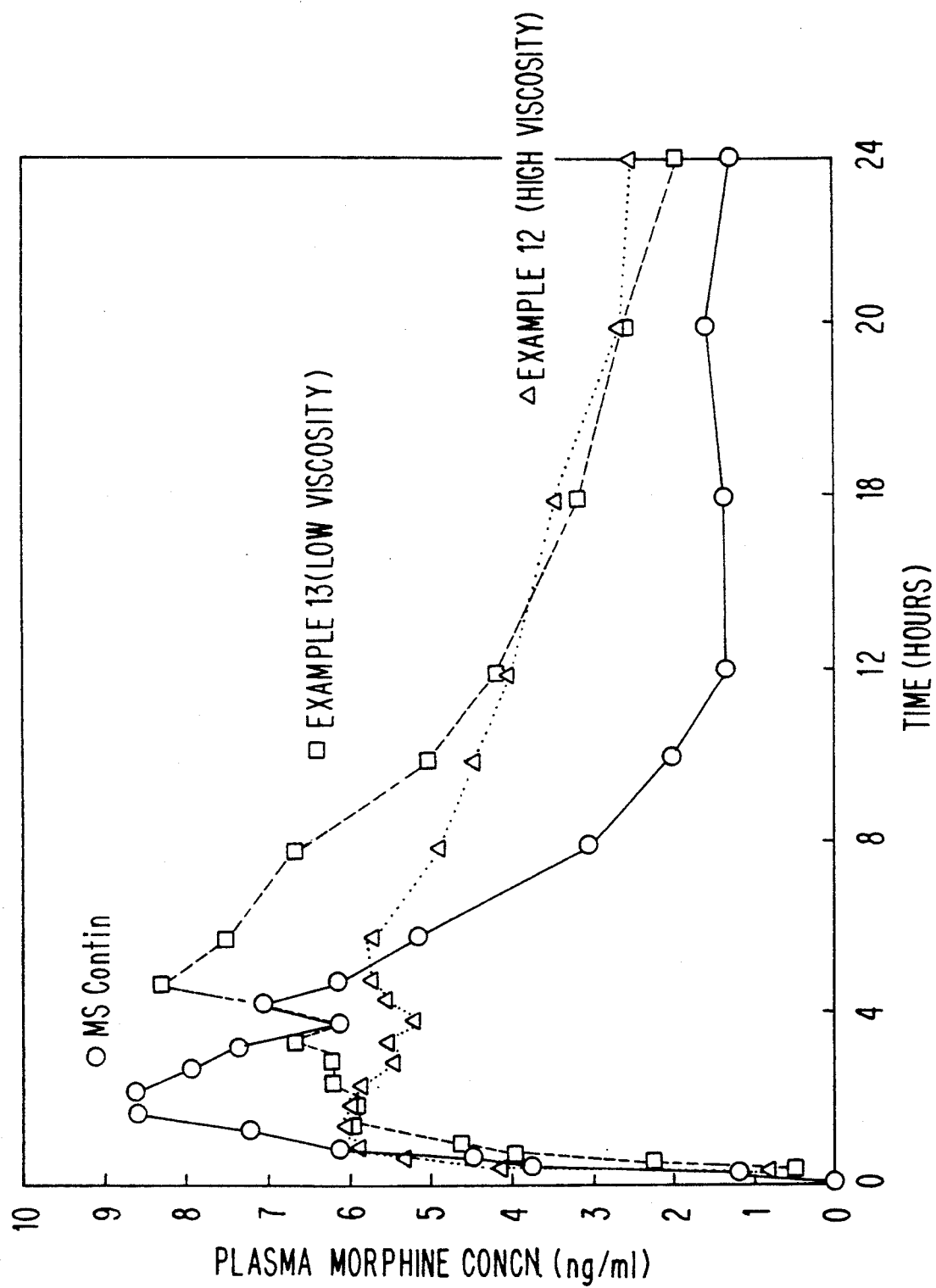

CONTROLLED RELEASE MATRIX SUPPOSITORY FOR PHARMACEUTICALS

Sustained release dosage forms are central in the search for improved therapy, both through improved patient compliance and decreased incidences of adverse drug reactions. Ideally, a controlled release dosage form will provide therapeutic concentration of the drug in blood that is maintained throughout the dosing interval with a reduction in the peak/nadir concentration ratio. Central to the development process are the many variables that influence the in-vivo release and subsequent absorption of the active ingredients from the gastrointestinal tract.

Controlled release formulations known in the art include specially coated beads or pellets, coated tablets and ion exchange resins, wherein the slow release of the active drug is brought about through selective breakdown of the coating of the preparation or through formulation with a special matrix to affect the release of the drug. Some controlled release formulations provide for sequential release of a single dose of an active medicament at predetermined periods after administration.

It is the aim of all controlled release preparations to provide a longer duration of pharmacological response after the administration of the dosage form than is ordinarily experienced after the administration of an immediate release dosage form. Such extended periods of response provides for many inherent therapeutic benefits that are not achieved with short acting, immediate release products. Thus, therapy may be continued without interrupting the sleep of the patient, which is of special importance when treating an epileptic patient to prevent nocturnal seizures, or patients with pain who experience severe pain on awakening, as well as for debilitated patients for whom an uninterrupted sleep is essential.

Another critical role for extending the duration of action of medications is in therapy of cardiovascular diseases wherein optimal peak blood levels of a medication must be maintained at steady state level in order to achieve the desired therapeutic effect. Unless conventional immediate release dosage forms are carefully administered at frequent intervals, peaks and valleys in the blood level of the active drug occur because of the rapid absorption and systemic excretion of the compound and through metabolic inactivation, thereby producing special problems in maintenance therapy of the patient. A further general advantage of longer acting drug preparations is improved patient compliance resulting from the avoidance of missed doses through forgetfulness.

The prior art teaching of the preparation and use of compositions providing for controlled release of an active compound from a carrier is basically concerned with the release of the active substance into the physiologic fluid of the alimentary tract. However, it is generally recognized that the mere presence of an active substance in the gastrointestinal fluids does not, by itself, insure bioavailability. Bioavailability, in a more meaningful sense, is the degree, or amount, to which a drug substance is absorbed into the systemic circulation in order to be available to a target tissue site.

To be absorbed, an active drug substance must be in solution. The time required for a given proportion of an active drug substance contained in a dosage unit to enter into solution in appropriate physiologic fluids is known as the dissolution time. The dissolution time of an active substance from a dosage unit is determined as the proportion of the amount of active drug substance released from the dosage unit over a specified time by a test method conducted under standardized conditions. The physiologic fluids of the gastrointestinal tract are the media for determining dissolution time. The present state of the art recognizes many satisfactory test procedures to measure dissolution time for pharmaceutical compositions, and these test procedures are described in official compendia world wide.

Although there are many diverse factors which influence the dissolution of a drug substance from its carrier, the dissolution time determined for a pharmacologically active substance from a specific composition is relatively constant and reproducible. Among the different factors affecting the dissolution time are the surface area of the drug substance presented to the dissolution solvent medium, the pH of the solution, the solubility of the substance in the specific solvent medium, and the driving forces of the saturation concentration of dissolved materials in the solvent medium. Thus, the dissolution concentration of an active drug substance is dynamically modified in this steady state as components are removed from the dissolution medium through absorption across the tissue site. Under physiological conditions, the saturation level of the dissolved materials is replenished from the dosage form reserve to maintain a relatively uniform and constant dissolution concentration in the solvent medium, providing for a steady state absorption.

The transport across a tissue absorption site in the gastrointestinal tract is influenced by the Donnan osmotic equilibrium forces on both sides of the membrane, since the direction of the driving force is the difference between the concentrations of active substance on either side of the membrane, i.e. the amount dissolved in the gastrointestinal fluids and the amount present in the blood. Since the blood levels are constantly being modified by dilution, circulatory changes, tissue storage, metabolic conversion and systemic excretion, the flow of active materials is directed from the gastrointestinal tract into the blood stream.

Notwithstanding the diverse factors influencing both dissolution and absorption of a drug substance. A strong correlation has been established between the in-vitro dissolution time determined for a dosage form and the in-vivo bioavailability. This correlation is so firmly established in the art that dissolution time has become generally descriptive of bioavailability potential for the active component of the particular dosage unit composition. In view of this relationship, it is clear that the dissolution time determined for a composition is one of the important fundamental characteristics for consideration when evaluating controlled release compositions.

Certain controlled release pharmaceutical compositions for oral administration consisting of a release matrix of sodium alginate and calcium salts have been discussed in the art. For example, in vitro evaluations of floating alginate gel-systems consisting of sodium alginate, calcium phosphate, sodium bicarbonate, drug and diluent filled in a gelatin capsule have been reported by Protan. Protan also reports that a method for treatment of diabetes by encapsulating islets of Langerhans in calcium alginate beads coated with a semi-permeable membrane have been developed.

However, less attention has been paid to the production of formulations where the route of administration is other than oral or where the active drug is highly water soluble. In situations where a drug cannot be taken orally, or where the physical condition does not permit oral administration, an alternate route of administration with a similar controlled release profile as the oral route is highly desirable.

In addition, improvements in the controlled release of therapeutically active agents from matrices of calcium salts/sodium alginates are also desirable.

SUMMARY OF THE INVENTION

An object of the present invention is to provide a new controlled release matrix which extends the time of release of active medicaments incorporated therein.

It is another object of the present invention to provide controlled release matrix compositions which are useful for all types of pharmaceutically active ingredients and which can extend the time of release of all such ingredients.

It is yet another object of the present invention to provide a controlled release matrix useful in rectal formulations.

In accordance with the above objects and other, the present invention is directed to controlled release compositions for the controlled release of therapeutically active ingredients over a pre-determined period of time, e.g. from five hours to as much as 24 hours after administration in human or animals.

More particularly, the present invention is related to a controlled release pharmaceutical composition for rectal administration, comprising a controlled release matrix comprising a pharmaceutically acceptable sodium alginate and a pharmaceutically acceptable calcium salt, a therapeutically active agent, and a suitable vehicle which melts or dissolves in rectal fluids. The calcium salt cross-links with the sodium alginate when the vehicle dissolves or melts, or when the components are exposed to aqueous solutions. Thereby, the release of the therapeutically active agent from the composition is controlled.

The present invention is also related to a controlled release pharmaceutical composition for oral administration, comprising a controlled release matrix comprising a pharmaceutically acceptable sodium alginate, a pharmaceutically acceptable calcium salt which cross-links with the sodium alginate when the composition is exposed to aqueous solutions, an effective amount of a higher aliphatic alcohol, and an effective amount of an active agent distributed or suspended in said controlled release matrix. The amount of higher aliphatic alcohol included is sufficient to obtain a desired rate of release of the active agent. The higher aliphatic alcohol preferably contains from about 8 to about 18 carbon atoms.

The present invention is further related to a controlled release matrix for the release of an orally administered therapeutically active agent, comprising from about 10 to about 50 percent by weight of a pharmaceutically acceptable sodium alginate, a sufficient amount of a pharmaceutically acceptable calcium salt to cross-link with the sodium alginate when the matrix is exposed to aqueous solutions or gastric fluid, and an effective amount of a higher aliphatic alcohol to obtain a desired rate of release of an active agent to be incorporated into the matrix.

The present invention is also related to a method for providing a controlled release suppository containing a pharmaceutically active agent, comprising combining a pharmaceutically acceptable sodium alginate, a pharmaceutically acceptable calcium salt in an amount effective to cross-link with the sodium alginate, and an effective amount of a therapeutically active agent, and then adding the mixture to sufficient quantity of a suitable melted vehicle. Suppositories are then prepared by pouring the mixture into molds and cooling.

The present invention is further related to a method of providing an orally administered controlled release composition for a therapeutically active agent, comprising preparing a controlled release matrix by combining a pharmaceutically acceptable sodium alginate with a pharmaceutically acceptable calcium salt capable of cross-linking the sodium alginate when exposed to aqueous solutions, a higher aliphatic alcohol, and an effective amount of a therapeutically active agent, such that the therapeutically active agent is suspended or distributed in the matrix, and including a sufficient amount of the calcium salt and higher aliphatic alcohol to control the release of said therapeutically active agent from the matrix at a desired rate when the composition is exposed to aqueous solutions.

BRIEF DESCRIPTION OF THE DRAWINGS

FIG. 1 is a graphical representation of mean plasma concentrations of morphine sulfate taken over a 24 hour period.

DETAILED DESCRIPTION

An important aspect of the present invention is related in part to the realization that a controlled release matrix for the oral administration of a wide variety of therapeutically active agents is obtained from the combination of a pharmaceutically acceptable sodium alginate, a pharmaceutically acceptable calcium salt, and a higher aliphatic alcohol.

Another important aspect of the present invention is directed to the discovery that controlled a release composition for rectal administration of a wide variety of drugs can be obtained from the combination of a pharmaceutically acceptable sodium alginate, a pharmaceutically acceptable calcium salt.

The bioavailability of rectally administered drugs is known to be erratic, and it is commonly the case that rectal absorption of a drug may be substantially different from absorption following oral administration.

Among the different factors affecting the dissolution time are the surface area of the drug substance presented to the dissolution solvent medium, the pH of the solution, the solubility of the substance in the specific solvent medium, and the driving forces of the saturation concentration of dissolved materials in the solvent medium. In the case of an orally administered drug, the physiologic fluids of the gastrointestinal tract are the media for determining dissolution time. Generally, factor affecting the absorption of drugs from suppositories administered rectally include anorectal physiology, suppository vehicle, absorption site pH, drug $pK_a$, degree of ionization, and lipid solubility.

Any pharmaceutically acceptable sodium alginate may be used in conjunction with the present invention the most preferred having a viscosity range between 10-500 cps as a one percent solution in water. More preferably, the alginate is a sodium alginate having a viscosity of from about 40 to about 150 cps as a one percent solution. In certain preferred embodiments the alginate has a viscosity from about 40 to about 70 cps as a one percent solution, for example when the matrix of the present invention is to be used in conjunction with a less soluble drug or when a faster dissolution profile is desired. In other embodiments, the alginate has a viscosity from about 70 to about 150 cps, for example when the drug to be incorporated is relatively water soluble or when a slow dissolution rate is desired. In yet other preferred embodiments, the sodium alginate has a viscosity from about 300 to about 500 cps as a one percent solution.

In terms of particle size, the sodium alginate preferably has a particle size from about 45 to about 125 microns, more preferably has a particle size of 70 microns or less.

Any alginates which are pharmaceutically acceptable can be used for the purposes of the present invention. Examples of commercially available alginates suitable for use in conjunction with the present invention are those that are marketed under the trade name "Protanal TM" and "Keltone TM", and are available from Protan A/S, Norway and Merck & Co. Inc., New Jersey, U.S.A. respectively.

The amount of alginate contained in the controlled release matrices and compositions of the present invention is dependent upon many factors, including the desired duration of action and the nature of the active drug substance to be incorporated into the composition. In general, the amount of alginate in the total composition is from about 10 to about 50 percent by weight and in certain embodiments more preferably from about 15 to about 30 percent by weight. The amount of alginate may be higher or lower depending upon the dosage regimen desired (once-a-day, twice-a-day, three-times-a-day, etc.).

Suitable calcium salts for use in the matrices and compositions of the present invention include calcium phosphate, dicalcium phosphate, calcium chloride, calcium carbonate, calcium acetate, and calcium gluconate. Other pharmaceutically acceptable calcium salts known in the art may also be used.

The amount of calcium salt in the compositions of the present invention must be sufficient to cross-link with the alginate when exposed to solutions (e.g. gastric fluid in the case of oral preparations, the melted base and rectal fluids in the case of a rectal preparation) such that a gel matrix is formed from which the drug is slowly released. Generally, in terms of the amount of sodium alginate in the composition, the amount of calcium salt is from about 2 to about 12 percent, and more preferably from about 8 to about 12 percent, by weight of the amount of sodium alginate present in the composition. In terms of the composition, the amount of calcium is generally from about 1 to about 4 percent, by weight.

Although it is preferred that calcium salts be used in the present invention, salts of other multivalent ions may be used instead such as $Al^{3+}$.

Generally, the controlled release compositions of the present invention provide sustained release of the drug(s) over a predetermined or a specified period of time, e.g. over a period of time from about 4–5 hours to as much as 24 hours after administration in humans or animals.

The controlled release compositions of the present invention for oral administration comprise a sodium alginate, a calcium salt and a higher aliphatic alcohol containing from 8 to 18 carbon atoms, which is optionally substituted by a further aliphatic group containing from about 8 to about 18 carbon atoms. The controlled release compositions of the present invention may be administered orally in the form of tablets, capsules, etc.

It is also contemplated that the compositions of the present invention may be adapted for buccal administration.

Examples of suitable higher aliphatic alcohols include fatty alcohols such as lauryl alcohol, myristyl alcohol, stearyl alcohol, cetyl alcohol and cetostearyl alcohol, and mixtures thereof.

The level of higher aliphatic alcohol in the oral compositions of the present invention is determined by the rate of drug release required. Generally, the compositions will contain from about 5% to about 45% (w/w), and preferably from about 10% to about 30% (w/w), of the higher aliphatic alcohol, as a proportion to the weight of the composition. The greater the amount of higher aliphatic alcohol included in the matrix, the slower the rate of release of the drug.

Upon oral ingestion and contact with fluids, the compositions of the present invention swell and gel to form a matrix from which the drug is released. Since the drug is suspended o distributed throughout the composition (and consequently throughout the matrix), a constant amount of drug can be released per unit time in vivo by dispersion or erosion of the outer portions of the matrix.

Any pharmaceutically accepted soluble or insoluble inert pharmaceutical filler (diluent) material can be used in the compositions of the present invention, such as monosaccharides, disaccharides, polyhydric alcohols, or mixtures thereof. Examples of inert diluents include sucrose, dextrose, lactose, microcrystalline cellulose, xylitol, fructose, sorbitol, mixtures thereof and the like. However, it is preferred that a soluble pharmaceutical filler such as lactose, dextrose, sucrose, or mixtures thereof be used.

In the case of tablets, an effective amount of any generally accepted pharmaceutical lubricant, including the calcium or magnesium soaps may be added to the above-mentioned ingredients of the excipient be added at the time the medicament is added, or in any event prior to compression into a solid dosage form. Most preferred is magnesium stearate in an amount of about 0.5–3% by weight of the solid dosage form.

In preparing the matrices of the present invention for oral administration, the sodium alginate, calcium salt, drug(s) and higher aliphatic alcohol can be combined together using a wet granulation technique of at least one step, to form a uniform granulate together with any of the other excipients that are required for the tableting or the capsule filling. Alternatively, the drug(s) can be combined during the process of preparing the granulate, or mixed with the granulate after it is prepared.

The moist granulated mass with or without the drug(s) is then dried and then the granulate is sized using a suitable screening device, which then provides a flowable powder which can then be filled into capsules or compressed into matrix tablets or caplets.

The controlled release matrix for rectal administration comprises sodium alginate and a calcium salt. The composition for rectal administration further comprises a drug and a suitable suppository vehicle (base). The suppository base chosen should of course be compatible with the drug(s) to be incorporated into the composition. Further, the suppository base is preferably nontoxic and nonirritating to mucous membranes, melts or dissolves in rectal fluids, and is stable during storage.

Prior to absorption, the drug must be in solution. In the case of suppositories, solution must be preceded by dissolution of the base, or the melting of the base and subsequent partition of the drug from the base into the rectal fluid.

The bioavailability of the drug can be altered by the suppository base. Thus, the particular base to be used in conjunction with a particular drug must be chosen giving consideration to the physical properties of the drug. For example, lipid-soluble drugs will not partition readily into the rectal fluid, but drugs that are only slightly soluble in the lipid base will partition readily into the rectal fluid.

In certain preferred embodiments of the present invention for both water-soluble and water-insoluble drugs, the suppository base comprises a fatty acid wax selected from the group consisting of mono-, di- and triglycerides of saturated, natural . fatty acids of the chain length $C_{12}$ to $C_{18}$.

In preparing the suppositories of the present invention other excipients may be used. For example, a wax may be used to suspend the alginate and calcium salt, as well as to form the proper shape for administration via the rectal route.

This system can also be used without wax, but with the addition of diluent filled in a gelatin capsule for both rectal and oral administration.

Examples of suitable commercially available mono-, di- and triglycerides include saturated natural fatty acids of the 12-18 carbon atom chain sold under the trade name Novata TM (types AB, AB, B,BC, BD, BBC, E, BCF, C, D and 299), manufactured by Henkel, and Witepsol TM (types H5, H12, H15, H175, H185, H19, H32, H35, H39, H42, W25, W31, W35, W45, S55, S58, E75, E76 and E85), manufactured by Dynamit Nobel.

Other pharmaceutically acceptable suppository bases may be substituted in whole or in part for the above-mentioned mono-, di- and triglycerides. The amount of base in the suppository is determined by the size (i.e. actual weight) of the dosage form, the amount of alginate and drug used. Generally, the amount of suppository base is from about 20 percent to about 90 percent by weight of the total weight of the suppository. Preferably, the amount of base in the suppository is from about 65 percent to about 80 percent, by weight of the total weight of the suppository.

In preparing the matrices of the present invention for rectal administration, the sodium alginate and calcium salt may be combined together with the drug. Thereafter, the suppository base can be melted, and the mixed powder added to the melted base and mixed. The uniform mixture is then poured into suppository shells, and the suppositories cooled.

The therapeutically active agents which may be used in the compositions of the present invention include a wide variety of drugs, including both water-soluble and water-insoluble drugs.

Examples of different classes of therapeutically active pharmaceutical agents that can be incorporated into the matrices of the present invention include antihistamines (e.g., dimenhydrinate, diphenhydramine (50-100 mg), chlorpheniramine and dexchlorpheniramine maleate), analgesics (e.g., aspirin, codeine, morphine (15-300 mg), dihydromorphone, oxycodone, etc.), anti-inflammatory agents (e.g., naproxyn, diclofenac, indomethacin, ibuprofen, acetaminophen, aspirin, sulindac), gastro-intestinals . and anti-emetics (e.g., metoclopramide (25-100 mg)), anti-epileptics (e.g., phenytoin, meprobamate and nitrezepam), vasodilators (e.g., nifedipine, papaverine, diltiazem and nicardipine), anti-tussive agents and expectorants (e.g., codeine phosphate), anti-asthmatics (e.g. theophylline), anti-spasmodics (e.g. atropine, scopolamine), hormones (e.g., insulin, heparin), diuretics (e.g., ethacrynic acid, bendroflumethiazide), anti-hypotensives (e.g., propranolol, clonidine), bronchodilators (e.g., albuterol), anti-inflammatory steroids (e.g., hydrocortisone, triamcinolone, prednisone), antibiotics (e.g., tetracycline), antihemorrhoidals, hypnotics, psychotropics, antidiarrheals, mucolytics, sedatives, decongestants, laxatives, antacids, vitamins, stimulants (including apetite suppressants such as phenylpropanolamine). The above list is not meant to be exclusive.

DESCRIPTION OF PREFERRED EMBODIMENTS

The following examples are given to further illustrate the present invention. The scope of the invention is not, however, meant to be limited to the specific details of the examples.

EXAMPLES 1-3

Morphine was tested in the controlled release system of the invention. The following three suppository formulations set forth in Table 1 demonstrate the principle of the invention with regard to a controlled release morphine suppository containing 30 mg active ingredient, the applicability and the advantages for pharmaceutical use.

TABLE 1

Morphine Suppository Formulations

| INGREDIENT | EXAMPLE 1 | 2 | 3 |
|---|---|---|---|
| Morphine Sulphate .5H$_2$O | 30.0 mg | 30.0 mg | 30.0 mg |
| Sodium Alginate (low viscosity LF grade) | 327.5 mg | 409.5 mg | 450.0 mg |
| DiCalcium phosphate | 32.5 mg | 40.5 mg | 45.0 mg |
| Novata-B | 1410.0 mg | 1320.0 mg | 1275.0 mg |
| Total | 1800.0 mg | 1800.0 mg | 1800.0 mg |

Novata-B is a mixture of mono-, di- and triglycerides based on saturated natural fatty acids of the chain lengths $C_{12}$ to $C_{18}$, with a specific melting range (33.4° C.-25.5.C).

The suppositories were prepared according to the following method: morphine sulphate powder, sodium alginate and calcium phosphate were all passed through a #200 sieve, individually. All three powders were intimately mixed in a suitable mixing apparatus. Novata B was melted in a stainless steel pot, keeping the temperature below 60° C.

The mixed powder was then added to the completely melted wax (around 50° C.) with constant stirring. The temperature was then cooled slowly to 40° C. and kept constant at that temperature. The uniform suspension was then transferred to a automated suppository filing kettle, and continuously stirred at 38° C.

After the fill weight was determined, the suppository shells were filled to the suggested fill weight at a temperature of about 37° C. (e.g., between 36°-38° C.). The suppositories were allowed to cool, then sealed.

Dissolution results were then conducted using USP basket method, 50 rpm, in phosphate buffer at pH 6.8. The results are set forth in Table 2.

TABLE 2

| | PERCENT MORPHINE SULPHATE DISSOLVED | | |
|---|---|---|---|
| Hour | Formulation A | Formulation B | Formulation C |
| 1 | 35.0 | 21.7 | 21.8 |
| 2 | 49.5 | 45.5 | 30.2 |
| 3 | 74.4 | 50.6 | 42.4 |
| 4 | 89.5 | 63.4 | 45.7 |
| 6 | 100.0 | 80.1 | 60.6 |
| 8 | — | 90.5 | 70.1 |
| 10 | — | 100.0 | 83.0 |
| 12 | — | — | 92.7 |

In Example 1, the amount of alginate was about 18.2% the amount of calcium salt was about 1.81%, and the amount of glyceride was about 78%, by weight of the composition In Example 2, the amount of alginate was about 22.75% the amount of calcium salt was about 2.25% and the amount of glyceride was about 73.33% by weight of the composition.

In Example 3, the amount of alginate was about 25%, the amount of calcium salt was about 2.5%, and the amount of glyceride was about 70.83%, by weight of the composition.

From the above dissolution results, as it can been seen that by increasing the proportions of sodium alginate and calcium phosphate, the release of morphine sulphate can be extended, e.g. to 6 to 12 hours.

EXAMPLES 4 and 5

Effect of Different Alginates

The usefulness of the invention was further demonstrated by the preparation of morphine suppositories using different viscosity grade of alginates.

The following two formulations set forth in Table 3 were prepared using the same method described for Examples 1–3. Each composition included 22.5% alginate, 2.25% calcium salt, and 73.33% glyceride.

TABLE 3

| | Example 4 | Example 5 |
|---|---|---|
| Morphine Sulphate .5H$_2$O | 30.0 mg | 30.0 mg |
| Protanal LF (Low Viscosity) | 405.0 mg | — |
| Protanal SF (High Viscosity) | — | 405.0 mg |
| Calcium Phosphate Dibasic | 45.0 mg | 45.0 mg |
| Novata B | 1320.0 mg | 1320. mg |
| Total Weight | 1800.0 mg | 1800.0 mg |

Dissolution results the results are set forth in for Examples 4 and 5 were then obtained using the U.S.P. basket method 50 rpm, in pH 6.8 Phosphate buffer.

TABLE 4

| | Percent Morphine Sulphate Dissolved | |
|---|---|---|
| Hour | Example 4 | Example 5 |
| 1 | 19.3 | 15.6 |
| 2 | 32.8 | 25.1 |
| 3 | 45.8 | 37.0 |
| 4 | 57.8 | 43.0 |
| 6 | 78.7 | 64.9 |
| 8 | 88.0 | 71.2 |

When comparing the dissolution results of suppositories A and B, it was observed that by using a high viscosity alginate, the release profile was sustained for a significantly longer period of time.

EXAMPLES 6–8

Varying amount of Drug

In Examples 6–8, controlled release suppositories of morphine sulphate were prepared in which the amount of drug is 30 mg, 60 mg and 100 mg, respectively. The following suppository formulations set forth in Table 5 (using the method described under Examples 1–3 above) were prepared.

TABLE 5

| | Example 6 | Example 7 | Example 8 |
|---|---|---|---|
| Morphine Sulphate .5H$_2$O | 30 mg | 60 mg | 100 mg |
| Protanal SF 200 | 405 mg | 360 mg | 360 mg |
| Calcium Phosphate Dibasic | 45 mg | 36 mg | 36 mg |
| Novata B | 1320 mg | 1344 mg | 1304 mg |
| Total | 1800 mg | 1800 mg | 1800 mg |

In Example 6, the composition included 22.5% alginate, 2.25% calcium salt, and 73.33% glyceride.

In Example 7, the composition included 20% alginate, 2% calcium salt, and 74.66% glyceride.

In Example 8, the composition included 20% alginate, 2% calcium salt, and 72.44% glyceride.

The suppositories of Examples 6–8 were then tested for dissolution using the USP basket method, 50 rpm, in pH 6.8 Phosphate buffer for 8 hours. The dissolution results are set forth in Table 6 below.

TABLE 6

| | PERCENT MORPHINE SULPHATE DISSOLVED | | |
|---|---|---|---|
| Hour | Example 6 | Example 7 | Example 8 |
| 1 | 14.45 | 17.15 | 16.58 |
| 2 | 22.57 | 30.68 | 25.43 |
| 3 | 33.00 | 40.36 | 35.80 |
| 4 | 43.56 | 48.85 | 42.81 |
| 6 | 57.23 | 65.08 | 56.35 |
| 8 | 65.88 | 69.67 | 68.55 |

Thus, different strengths of morphine suppositories with controlled release characteristics can be manufactured by varying the proportions of the different ingredients in the controlled release system of the present invention.

EXAMPLES 9–11

ORAL CONTROLLED RELEASE SYSTEM

An oral controlled release composition according to the present invention was prepared with the formulation set forth in Table 7.

TABLE 7

| Ingredient | Weight (mg) |
|---|---|
| Dimenhydrinate | 75 |
| Protanol SF/200 (Sodium Alginate) | 75 |
| Calcium Phosphate | 7 |
| Lactose (spray dried) | 25 |
| Cetostearyl Alcohol | 30 |
| Magnesium Stearate | 3 |
| Talc | 3 |
| Total | 218 mg |

The dimenhydrinate, protanol, calcium phosphate and lactose were dry blended until thoroughly mixed. Cetostearyl alcohol was added to the warmed mixed powder, and the whole was mixed thoroughly. The mixture was allowed to cool in the air, regranulated and sieved through a 16 mesh screen.

The coated granules were filled in a hard gelatin capsule using talc and magnesium stearate as lubricants (capsules) or were compressed using appropriate punches (tablets).

Dissolution studies of Example 9, using USP paddle method, 50 rpm were then obtained in deionized water. Representative results for both tablets and capsules are set forth in Table 8.

TABLE 8

| Hour | Percent of Dimenhydrinate Dissolved |
|---|---|
| 1 | 15.00 |
| 2 | 29.00 |
| 3 | 47.00 |
| 4 | 70.00 |
| 5 | 77.00 |
| 6 | 91.00 |

In Example 10, the method of Example 9 was followed, except that the amount of cetostearyl alcohol was increased to 50 mg per capsule or tablet. Dissolution results of Example 10, using USP paddle method, 50 rpm were then obtained in deionized water. Representative results for the capsules and tablets ar set forth in Table 9.

TABLE 9

| Hour | Percent of Dimenhydrinate Dissolved |
|---|---|
| 1 | 25.00 |
| 2 | 34.00 |
| 3 | 38.00 |
| 4 | 53.00 |
| 6 | 71.00 |

In Example 11, the method of Example 9 was followed except the amount of dimenhydrinate was decreased to 50 mg and the amount of lactose increased to 70 mg. Dissolution results of Example 11, using USP paddle method, 50 rpm were then obtained in deionized water. Representative results for the capsules and tablets are set forth in Table 10.

TABLE 10

| Hour | Percent of Dimenhydrinate Dissolved |
|---|---|
| 1 | 22.00 |
| 2 | 47.00 |
| 3 | 82.00 |
| 4 | 92.00 |
| 6 | 100.00 |

EXAMPLES 12-13

Bioavailability Comparison of Two Controlled Release Morphine Rectal Suppository Formulations A three-way crossover bioavailability study was conducted to compare two 30 mg morphine sulfate controlled release rectal suppositories. Example 12 was formulated according to Example 5 (high viscosity alginate) and Example 13 was formulated according to Example 4 (low viscosity alginate) with the marketed MS Contin mg tablet given orally.

Fourteen (14) healthy male volunteers received single 30 mg doses of each of the two suppositories and MS Contin in randomized order separated by a washout period of one week. In all phases, subjects maintained a reclining position for 1 hour and fasted for 4 hours following the dose. Preceding each rectal administration subjects were administered a Fleet enema and underwent proctoscopic examinations before dosing and at the end of the blood sampling period. Blood samples were drawn prior to each dose and at 0.25, 0.5, 0.75, 1, 1.5, 2, 2.5, 3, 3.5, 4, 5, 6, 8, 10, 12, 16 and 24 hours after the dose. Plasma was analyzed by a RIA method using antibodies that did not cross-react with the glucuronide metabolites. Mean plasma concentrations at each sampling time are depicted graphically in FIG. 1.

Both suppositories produced excellent sustained release profiles. For Suppositories A and B, maximum plasma concentrations (Cmax) were 7.8 and 9.2 mg/ml respectively, compared to 10.4 mg/ml for MS contin. Curve width at half maximum plasma concentration ($W_{50}$) was approximately 10 hours for both suppositories versus 4.3 hours for MS Contin. Overall bioavailability (AUC 0-24) was 39% greater than MS Contin for Example 12 and 44% higher for Example 13. This increased bioavailability is possibly the result of avoidance or reduction of the "first-pass" effect Between-subject variability in bioavailability was greater for both suppository formulations than for orally-administered MS Contin tablets.

No serious or unexpected adverse reactions were noted for any of the formulations. Adverse experiences were reported in 2 subjects following Example 12, in 6 subjects after Example 13, and in 4 subjects after MS Contin (Table 2). The post-dose proctoscopic findings were limited to mild erythema in 6 subjects following Example 12 and 5 subjects after Example 13 (for two of these latter subjects, mild erythema was also reported pre-dose).

Based on the foregoing results, either suppository would be suitable formulation. The effects of the difference in alginate viscosity between the two suppository formulations appeared to be primarily limited to Cmax, in that, for the high viscosity Example 12, Cmax was approximately 85% of that observed with Example 13. Since side effects may have been associated with the higher peak concentration of Example 13 and, at steady state, peak concentrations will be even higher, it is considered that the formulation with the lower Cmax (Example 12) may offer a greater margin of safety.

While the invention has been illustrated with respect to the foregoing examples, different drugs, alginic acids, salts of multivalent ions and excipients (including suppository bases) can be substituted. Such variations and modifications thereof can be made without departing from the spirit and scope of the invention, and are contemplated to be within the scope of the appended claims.

What is claimed is:

1. A controlled release pharmaceutical suppository for rectal administration in humans or animals, comprising
   a controlled release matrix consisting essentially of a pharmaceutically acceptable sodium alginate and a pharmaceutically acceptable calcium salt selected from the group consisting of calcium phosphate, dicalcium phosphate, calcium chloride, calcium carbonate, calcium acetate, calcium gluconate, and mixtures of any of the foregoing,
   a therapeutically active agent, and
   a suitable vehicle which melts or dissolves in rectal fluids, said calcium salt being in an amount sufficient to cross-link with the sodium alginate and thereby provide a controlled release of said therapeutically active agent from said matrix when said vehicle melts or dissolves.

2. The composition of claim 1, wherein the sodium alginate comprises from about 10 to about 50 percent of said composition by weight, and the amount of calcium salt is from about 2 to about 12 percent by weight of the sodium alginate in the composition.

3. The composition of claim 1, wherein said vehicle is a fatty acid wax selected from the group consisting of mono-, di- and triglycerides of saturated, natural fatty acids of the chain length $C_{12}$ to $C_{18}$.

4. The composition of claim 3, wherein said vehicle comprises from about 20 to about 90 percent of said composition, by weight.

5. The composition of claim 3, wherein said vehicle comprises from about 65 to about 80 percent of said composition, by weight.

6. The composition of claim 5, wherein the sodium alginate comprises from about 15 to about 30 percent of said composition by weight.

7. The composition of claim 1, wherein the sodium alginate has a viscosity from about 40 to about 150 cps as a 1 percent solution.

8. The composition of claim 1, wherein the sodium alginate has a viscosity from about 300 to about 500 cps as a 1 percent solution.

9. The composition of claim 1, wherein the sodium alginate has a particle size from about 45 to about 125 microns.

10. A method for providing a controlled release suppository containing a pharmaceutically active agent for rectal administration in humans and animals, comprising combining a controlled release matrix consisting essentially of a pharmaceutically acceptable sodium alginate and a pharmaceutically acceptable calcium salt selected from the group consisting of calcium phosphate, dicalcium phosphate, calcium chloride, calcium carbonate, calcium acetate, calcium gluconate, and mixtures of any of the foregoing with an affective amount of a therapeutically active agent to provide a therapeutic effect, adding the mixture to a sufficient quantity of a suitable melted vehicle and then preparing suppositories, and including the calcium salt in an effective amount to cross-link the sodium alginate and thereby provide a controlled release of the therapeutically active agent when said vehicle melts or dissolves.

11. The composition of claim 1, wherein the calcium salt comprises from about 1 to about 4% by weight of the said composition.

12. The composition of claim 3, wherein said fatty acid wax has a melting point in the range of from about 29° C. to about 42° C.

13. The composition of claim 1, wherein said therapeutically active agent is amitriptyline, atropine, chlorpromazine, codeine, diclofenac, diphenhydramine, doxylamine, ephedrine, hyoscyamine, morphine, metoclopramide, hydromorphone, naproxyn, oxycodone, papaverine, phenyl-propanolamine, propanolol, quinidine, scopolamine, theophylline, or thioridazine.

* * * * *